United States Patent [19]
Yanagida et al.

[11] Patent Number: 5,602,324
[45] Date of Patent: Feb. 11, 1997

[54] GAS SENSOR AND GAS DISCRIMINATING METHOD

[75] Inventors: Hiroaki Yanagida, Tokyo; Masaru Miyayama, Kawasaki; Kazuyasu Hikita, Omiya, all of Japan

[73] Assignee: Mitsubishi Materials Corporation, Tokyo, Japan

[21] Appl. No.: 424,366

[22] PCT Filed: Oct. 3, 1994

[86] PCT No.: PCT/JP94/01650

§ 371 Date: Apr. 25, 1995

§ 102(e) Date: Apr. 25, 1995

[87] PCT Pub. No.: WO95/10039

PCT Pub. Date: Apr. 13, 1995

[30] Foreign Application Priority Data

Oct. 5, 1993 [JP] Japan .................... 5-249526
Feb. 25, 1994 [JP] Japan .................... 6-028125

[51] Int. Cl.⁶ .................... G01N 27/12; G01N 27/04; G01N 27/02
[52] U.S. Cl. .................... 73/23.2; 73/31.06
[58] Field of Search .................... 73/23.2, 31.05, 73/31.06; 338/34; 422/98

[56] References Cited

U.S. PATENT DOCUMENTS

| | | | |
|---|---|---|---|
| 2,975,362 | 3/1961 | Jacobson | 73/31.06 |
| 4,103,227 | 7/1978 | Zemel | 73/31.06 |

FOREIGN PATENT DOCUMENTS

| | | | |
|---|---|---|---|
| 575628 | 12/1993 | European Pat. Off. | 73/31.06 |
| 46498 | 4/1977 | Japan | 338/34 |
| 62-90528A | 4/1987 | Japan . | |
| 90529 | 4/1987 | Japan | 73/31.06 |
| 283002 | 11/1988 | Japan | 338/34 |
| 223660 | 10/1991 | Japan | 73/31.06 |
| 5-249064A | 9/1993 | Japan . | |

93/14396A 7/1993 WIPO .

OTHER PUBLICATIONS

S. Kanefusa, et al. Nihon Kagaku–Kaishi, No. 10, (1980) The Chemical Society of Japan, pp. 1591–1596 (1980).
Y. Nakamura, et al. "The Current Voltage Characteristics of CuO ZnO Heterojunctions", Nihon Kagaku–Kaishi, No. 6, pp. 1154–1159 (1985).
Y. Nakamura, et al. "The Detection of Carbon Monoxide by the Oxide–Semiconductor Hetero–Contacts" Nihon Kagaku–Kaishi, No. 3, pp. 477–483 (1987).
Y. Nakamura, et al. "Selective CO Gas Sensing Mechanism with CuO/ZnO Hetero–contact", J. Electrochem. Soc., vol. 137, No. 3, pp. 940–943 (1990).
F. Gutierrez, et al. "Properties of Polycrystalling Gas Sensors Based on d.c. and a.c. Electrical Measurements", Sensors and Actuators B, 8, pp. 231–235 (1992).

(List continued on next page.)

*Primary Examiner*—Hezron E. Williams
*Assistant Examiner*—Daniel S. Larkin
*Attorney, Agent, or Firm*—Ronald J. Kubovcik; Peter B. Martine

[57] ABSTRACT

The present invention relates to a gas sensor and a gas discriminating method which are capable of distinctly discriminating two or more kinds of gases. A DC bias and AC signals which are superposed to a junction part, which is formed on a gas sensor having a p-type oxide semiconductor and an n-type oxide semiconductor by means of heterojunction of end surfaces thereof, an impedance characteristic of the junction part is measured, and CO gas and $H_2$ gas are discriminated in accordance with a dependence on a frequency of the AC signals and on the DC bias of the impedance characteristic. CuO into which an alkali metal element is doped is used as the p-type oxide semiconductor and ZnO is used as the n-type oxide semiconductor. The alkali metal element to be used is an alkali metal element selected from the group of Li, Na and K and the doping quantity is such that $0.2$ mole $\% \leq M_2O \leq 5$ mole $\%$, where M is Li, Na or K.

9 Claims, 14 Drawing Sheets

OTHER PUBLICATIONS

T. Ishihara, et al. "Application of Mixed Oxide Capacitor to the Selective Carbon Dioxide Sensor", J. Electrochem, Soc., vol. 138, pp. 173–176 (1991) [11200].

T. Ishihara, et al. "Adsorption of Mixed Oxide Capacitor to the Selective Carbon Dioxide Sensor" J. Electrochem, Soc., vol. 139, 2881–2885.

Y. Ushio et al. "Effects of interface states on gas–sensing properties of a CuO/ZnO thin–film heterojunction", Sensors and Actuators B, 17 (1994) pp. 221–226.

H. Yanagida, "Intelligent Ceramics", Ferroelectrics, 1990, vol. 102, pp. 251–257 (1990).

Tetsuro Seiyama, "Chemical Sensors–Current State and Future Outlook", Chemical Sensor Technology, vol. 1, Kodansha and Elsevier (1988), pp. 1–13.

G. Heiland, et al. "Physical and Chemical Aspects of Oxidic Semiconductor Gas Sensors", Chemical Sensor Technology, vol. 1, Kodansha and Elsevier (1988), pp. 15–38.

Tetsuro Seiyama, "A New Detector for Gaseous Components Using Semiconductive Thim Films", Analytical Chemistry, 34 1502 (1962).

Norio Miura, et al. "Adsorption and Desorption Behavior of Oxygen on Semiconductive Metal Oxides", Denki–Kagaku.49, No. 6 (1981) pp. 367–368.

N. Ichinose, et al. Bull. Ceram. Soc. Jpn, 11, (1976) pp. 205–210.

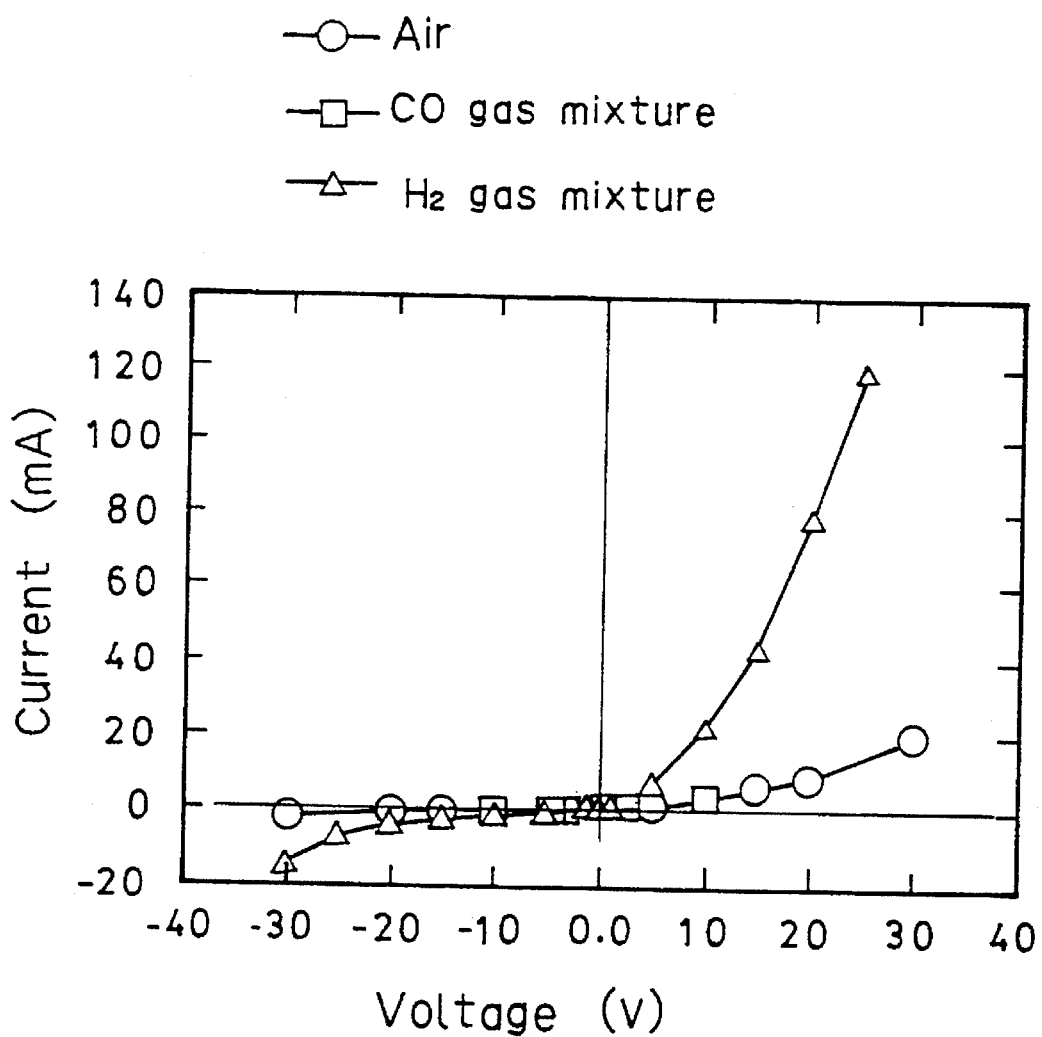

GAS SENSOR AND GAS DISCRIMINATING METHOD

FIELD OF THE INVENTION

The present invention relates to a gas sensor and a gas discriminating method.

BACKGROUND OF THE RELATED ART

Semiconductor gas sensors which can be used even in a high temperature corrosive atmosphere have been known and used for detecting poisonous gases under severe conditions (see "Chemical Sensor Technology", vol. 1, Kodansha and Elsevier (1988), pp 1–13, 15–38). This semiconductor gas sensor utilizes a principle that electrical conductivity on a surface of a semiconductor is changed by loading and unloading of electric charge which is carried out when chemical species are adsorbed onto and desorbed from the surface of the semiconductor (see Anal. Chem. 34 1502 (1962) "Adsorption and Desorption Behavior of Oxygen on Semiconductive Metal Oxides", Denki-Kagaku. 49. 367–368 (1981)). This semiconductor gas sensor is liable to react with various types of reducing gas and accordingly provides only an insufficient ability in discrimination of a plurality of reducing gases from one another. Catalysts have been used to improve this gas discriminating ability of the gas sensor (see Bull. Ceram. Soc. Jpn, 11,205 (1976), Nihon Kagaku-Kaishi, 1591 (1980). However, even though the catalysts are used, it has been difficult to discriminate, for example, hydrogen gas from carbon monoxide gas and therefore it has been considered that an important subject is to improve the ability for discriminating a gas to be measured (see "Ceramic Sensors", Kodansha (1984)).

A heterojunction type gas sensor which uses the p-n junction of the semiconductor has been studied to develop a gas sensor with a high gas discriminating ability. The sensing performance of this heterojunction type gas sensor to steam, combustible gases (for example, hydrogen, carbon monoxide gas, and propane), chlorine gas and nitrogen oxide gas has been investigated and studied (see "The Current Voltage Characteristics of CuO/ZnO Heterojunctions", Nihon-Kagaku-Kaishi, 1154–1159 (1985); "The Detection of Carbon Monoxide by the Oxide-Semiconductor Hetero-Contacts", Nihon-Kagaku-Kaishi, 477–483 (1987); "Selective CO Gas Sensing Mechanism with CuO/ZnO Hetero-contact", J. Electrochem. Soc., Vol. 137, No. 3, 940–943 (1990); "Effects of Interface States on Ga Sensing Properties of a CuO/ZnO Thin Film Heterojunction" (in printing); and "Intelligent Ceramics", Ferroelectrics, Vol. 102, 251–257 (1990)). These studies are intended to utilize a phenomenon that a value of a current which flows through the heterojunction is affected by an ambient atmospheric gas and measure a kind and a content of gas based on a voltage-current relationship obtained by applying a DC voltage to the heterojunction. These studies have reported that a heterojunction type gas sensor which provides a high sensitivity to carbon monoxide gas and hydrogen gas (particularly, carbon monoxide gas) can be made by combining cupric oxide (CuO; hereafter referred to as "copper oxide"), which is manufactured with basic copper carbonate as raw material, and zinc oxide (ZnO) (see "The Detection of Carbon Monoxide by the Oxide-Semiconductor Hetero-Contacts, Nihon-Kagaku-Kaishi, 477–483 (1990)). According to this report, it is described that the sensitivity of the heterojunction type gas sensor to carbon monoxide gas and hydrogen gas is raised when a forward biased specific voltage (0.5 V) is applied to the heterojunction and, though carbon monoxide gas cannot be discriminated from hydrogen gas only with this biasing, a CO density can be determined by calculation based on a difference between the sensitivity when the 0.5 V voltage is applied and the sensitivity when the other voltage (for example, 1.0 V) is applied if it is known in advance that two kinds of gases, that is, carbon monoxide gas and hydrogen gas are contained.

In these studies using the heterojunction type gas sensor, gases are discriminated based on the difference of the values of current which flows in the heterojunction when a certain specified voltage is applied to the heterojunction. However, this difference of the current value is extremely small and therefore some improvement is required for distinct discrimination of gases.

There have been several views as evaluation methods with respect to a sensing performance using DC characteristics, static capacity and impedance of a single ceramics semiconductor and those methods which can be used for the gas sensors (see "Properties of Polycrystalling Gas Sensors Based on d. c. and a. c. Electrical Measurements", Sensors and Actuators B, 8, 231–235 (1992); "Application of Mixed Oxide Capacitor to the Selective Carbon Dioxide Sensor", J. Electrochem, Sec., Vol. 138, 173–176 (1991) [11200]; and "Application of Mixed Oxide Capacitor to the Selective carbon Dioxide Sensor", J. Electrochem, Soc., Vol. 139, 2881–2885). However, examinations for using as the gas sensors which excel in gas discrimination performance are insufficient.

DISCLOSURE OF THE INVENTION

An object of the present invention made in view of the above-described problems is to provide a gas sensor and a gas discriminating method capable of more distinctly discriminating the kinds of gases.

A gas sensor according to the present invention for accomplishing the above object is characterized in that the gas sensor comprises a sensor head having a p-type oxide semiconductor and an n-type oxide semiconductor whose junction portions are formed by hetero junction process of their end faces, signal applying means for applying AC signals onto which a DC bias is superposed to the junction part, and impedance measuring means for measuring an impedance characteristic of the junction part.

In this case, the p-type oxide semiconductor and the n-type oxide semiconductor are preferably made of ceramics. Moreover, it is preferable that the p-type oxide semiconductor is CuO and the n-type oxide semiconductor is ZnO. In addition, the above CuO is preferably CuO into which an alkali metal is doped. It is preferable that this alkali metal is an alkali metal element selected from a group of Li, Na and K and a quantity of this alkali metal to be added is within the range of 0.2 mole $\% \leq M_2O \leq 5$ mole $\%$.

A first gas discriminating method according to the present invention for accomplishing the above object is characterized in that the DC bias and AC signals which are superposed are applied to the above-described junction portions of the gas sensor provided with the p-type oxide semiconductor and the n type oxide semiconductor whose junction portions are formed through the heterojunction process of their end faces, the impedance characteristics of the junction portions are measured, and the kinds of gases are discriminated based on the dependence property of the above-described impedance characteristics on the frequency of the AC signals and the DC bias.

Moreover, a second gas discriminating method according to the present invention is characterized in that the DC bias which makes the p-type oxide semiconductor negative and the n-type oxide semiconductor positive under a certain specified frequency is applied to the above-described junction portions of the gas sensor provided with the p-type oxide semiconductor and the n-type oxide semiconductor whose junction portions are formed through the heterojunction process of their end faces, the impedance characteristics of the junction portions are measured, and the kinds of gases are discriminated based on the dependence property of the reactance component of the above-described impedance characteristic on the DC bias.

Furthermore, a third gas discriminating method according to the present invention is characterized in that the DC bias which makes the p-type oxide semiconductor negative and the n-type oxide semiconductor positive and AC signals are applied to the above-described junction portions of the gas sensor provided with the p-type oxide semiconductor and the n-type oxide semiconductor whose junction portions are formed through the heterojunction process of their end faces, the impedance characteristics of the junction portions are measured by varying the frequency of AC signals, and the kinds of gases are discriminated based on the dependence property of the reactance component of the above-described impedance characteristic on the frequency of AC signals.

Furthermore, a fourth gas discriminating method according to the present invention is characterized in that the DC bias and AC signals which are superposed are applied to the above-described junction portions of the gas sensor provided with the p-type oxide semiconductor and the n-type oxide semiconductor whose junction portions are formed through the heterojunction process of their end faces, the impedance characteristics of the junction portions are measured, and $CO$ and $H_2$ gases are discriminated based on the dependence property of the above-described impedance characteristic on the frequency of the AC signals and the DC bias.

In this case, it is preferable to use a p-type oxide semiconductor made of $CuO$ as the above-described p-type oxide semiconductor and an n-type oxide semiconductor made of $ZnO$ as the above-described n type oxide semiconductor. It is preferable to use $CuO$ into which an alkali metal element is doped.

In the present invention, an electrical rectifying characteristic of a rectifying barrier (Schottky barrier) which is formed by heterojunction is noted with an emphasis. Since free electrons and free holes are diffused in bulk on the heterojunction surfaces of the p-type oxide semiconductor and the n-type oxide semiconductor, there are less free carriers and a transition boundary layer referred to as a depletion layer is formed. This transition boundary layer provides a rectifying action which facilitates the current flow when a forward bias is applied and does not substantially permit the current flow when a reverse bias is applied. Generally, electrical characteristics of the oxide semiconductor are affected when the oxide semiconductor adsorbs an atmosphere gas to cause formation of electric charge.

In the gas sensor according to the present invention, the heterojunction of the p-type oxide semiconductor and the n-type semiconductor is formed and this heterojunction is used to discriminate gases. The characteristics of adsorption of reducing gases ($CO$ and $H_2$) and oxygen differ with the type of semiconductor and consequently, the heterojunction of the p-type oxide semiconductor and the n-type oxide semiconductor is used in the gas sensor. This sensor can more distinctly discriminate a plurality of reducing gases (for example, $CO$ gas and $H_2$ gas) than the gas sensor which uses an oxide semiconductor made of a single component.

The present invention also lays another emphasis on the point that electrical rectifying characteristics, particularly an impedance characteristic, of the rectifying barrier which is formed by heterojunction can be positively used for improving the gas sensitivity and rendering discriminativity and selectivity of gases. In other words, though the depletion layer where the original electric charge of the semiconductor is insufficient since the rectifying barrier is formed on the heterojunction surface, it is assumed that a change of electric charge and a change of electrical conduction are keenly reflected due to adsorption of gas and therefore these changes may be effectively used in discrimination of gases. Accordingly, the inventor has examined a method capable of discriminating the kinds of gases based on the relationship between the impedance (frequency information) and the kinds of gases at the negative (reverse) bias side which has not been noted because of a small current value.

A change of capacity components and a change of a surface resistance due to adsorption of a gas differs with the kind of gas and therefore the gases can be discriminated by detecting these changes using AC signals with a negative bias where the resistance value is increased owing to rectifiability thereof. In a case that an alkali metal element is doped in $CuO$ which is the p-type semiconductor, the discrimination performance for $CO$ gas can be improved.

The gas sensor and the gas discrimination method according to the present invention enables one to more distinctly discriminate the kinds of gases, particularly, $CO$ gas and $H_2$ gas, the detection of which has been deemed difficult among reducing gases, than the prior art. The gas sensor provided with the sensor head having the junction part for $CuO$ and $ZnO$ is able to easily discriminate $CO$ gas and $H_2$ gas and, if an alkali metal is doped in $CuO$, more easily discriminate $CO$ gas and $H_2$ gas.

As described above, according to the present invention: (1) Since the kinds of gases can be discriminated by applying the DC bias and AC signals which are superposed to the heterojunction and applying a negative bias under a certain specified frequency or scanning the frequency under the negative bias applied, two or more kinds of gases can be discriminated by one gas sensor without using multiple kinds of sensors. (2) A combustible mixed gas ($CO$ and $H_2$) can be discriminated distinctly and easily with one sensor. (3) In a case that the p-type oxide semiconductor made of $CuO$ to which an alkali metal element is doped is used, a gas sensor which provides a high $CO$ gas discriminating ability at a lower temperature than in a case that pure $CuO$ is used can be obtained.

BRIEF DESCRIPTION OF THE DRAWINGS

FIG. 3 is a graph of a comparison example showing the rectifying characteristics at 400° C. by means of the p-n heterojunction of $CuO/ZnO$;

BEST MODE FOR CARRYING OUT THE INVENTION

The present invention is described below in detail referring to the accompanying drawings.

[First Embodiment]

(a) Specimen

Figure 1:
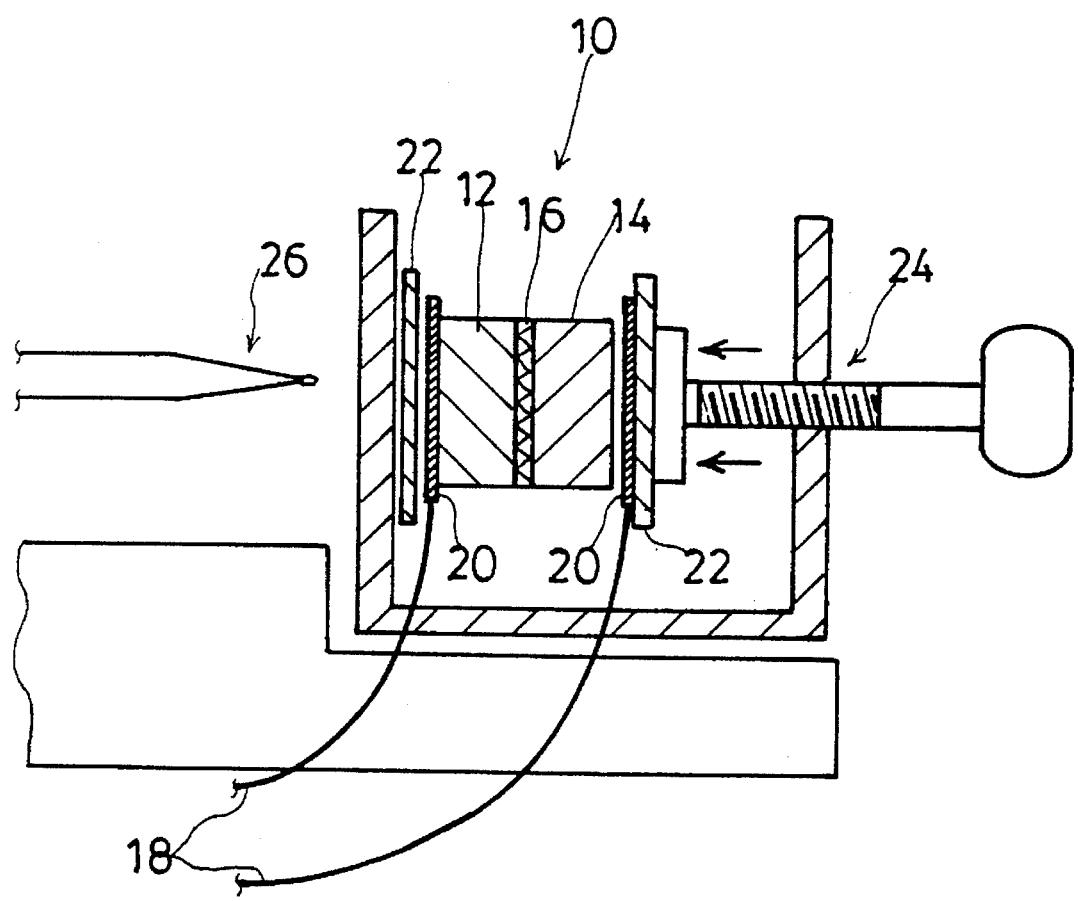
FIG. 1 is a diagram showing the manufacturing processes for the sensor head of the gas sensor according to the present invention.

Referring to FIG. 1, a specimen to be used as a sensor head of a gas sensor is described below.

Powder of ZnO (99.99%) is formed into a disc with a diameter of 10 mm and a thickness of approximately 1 mm after granulating the powder by a PVA binder and this disc is fired at 1000° C. for 3 hours to obtain a disc type specimen 12 of n-type semiconductor. Powder of CuO (99.99%) is formed into a disc with a diameter of 10 mm and a thickness of approximately 1 mm after granulating the powder by a PVA binder and this disc is fired at 800° C. for 3 hours to obtain a disc type specimen 14 of p-type semiconductor. The relative densities of these specimens 12 and 14 are 98% as ZnO and 90% as CuO.

A silver electrode with an ohmic characteristic is baked on one-side surfaces of respective n-type and p-type semiconductor disc type specimens 12 and 14 which are ground to be parallel with an emery paper (#1000) and these specimens are joined together to form a heterojunction 16. Subsequently, as shown in FIG. 1, platinum electrode plates 20 to which a lead wire 18 is respectively connected are attached to these specimens 12 and 14 and a heterojunction surface made of p-type/n-type semiconductors is formed by mechanically tightening the specimens through insulation sheets 22 with a stainless steel holder 24. Thus a sensor head 10 having the p-type/n-type semiconductors is made. A thermocouple 26 is prepared to measure a temperature of the sensor head 10.

(b) Measuring Method

Figure 2:
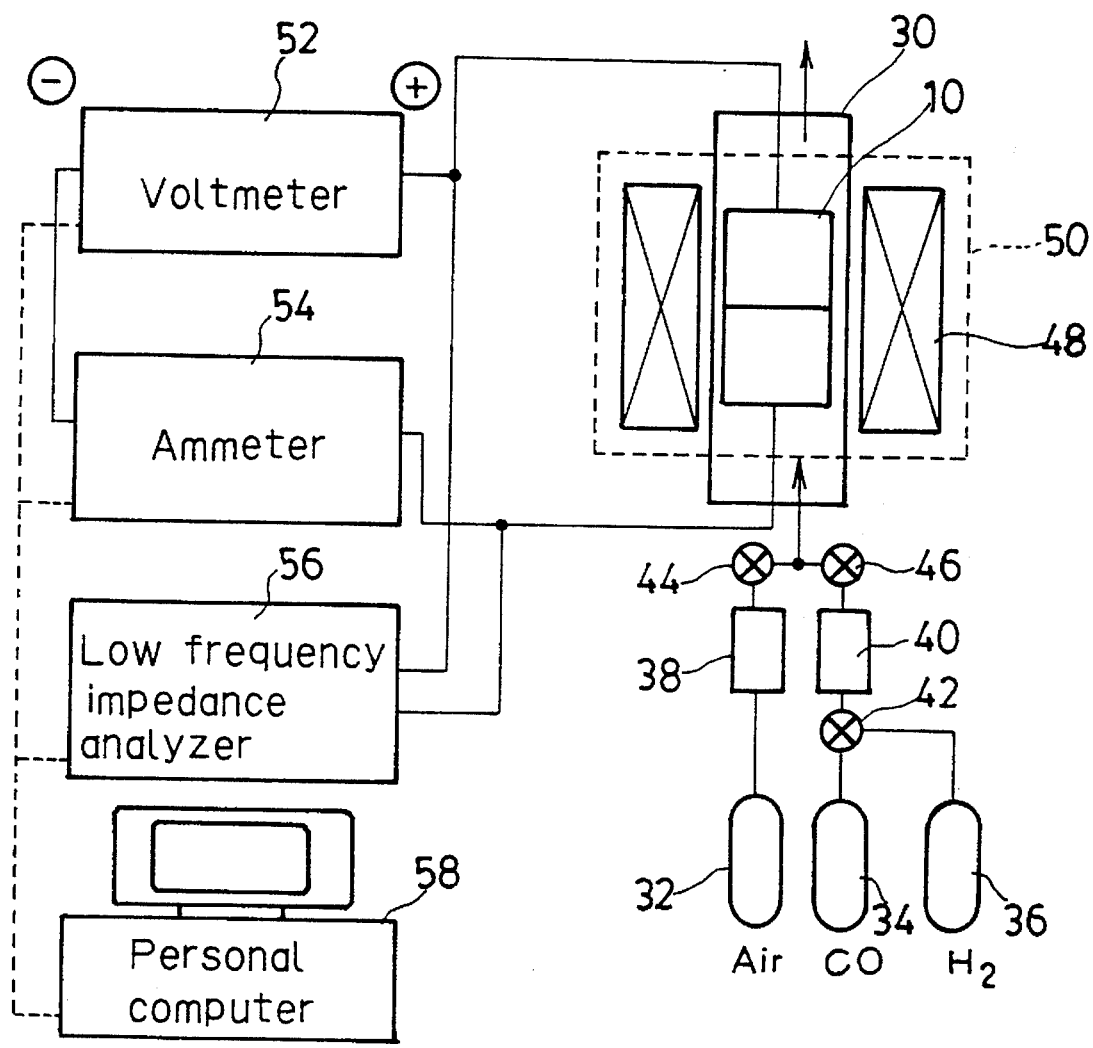
FIG. 2 is a block diagram showing a schematic configuration of an embodiment of the gas sensor according to the present invention.

A construction of the gas sensor is described referring to FIG. 2. The sensor head 10 is set in a ceramics tube 30 and air, a mixture of air and CO gas (4000 ppm) and a mixture of air and $H_2$ gas (4000 ppm) are separately let to flow into the ceramics tube 30 at a flow rate of 200 ml/min (room temperature). The air, CO gas and $H_2$ gas are separately introduced into the ceramics tube 30 from respective gas cylinders 32, 34 and 36 through flow meters 38 and 40 and valves 42, 44 and 46. The sensor head 10 is heated in a range of room temperature to 400° C. in a furnace 50 provided with a heater 48. Under a condition where the sensor head 10 is maintained at, for example, 400° C., the gases described above are introduced and DC voltage/current characteristic (HP) and a DC bias are applied to the sensor head 10. The voltage and current of the sensor head 10 are measured by a voltmeter (YOKOGAWA 7651) 52 and an ammeter (YOKOGAWA 7652) 54 and a complex impedance (HP4192A) is measured by using a low frequency impedance analyzer 56. These units of measuring equipment are controlled by a personal computer 58, and a resistance component (R) and a reactance component (X) of the complex impedance Z (=R+jX) are measured from 0.01 kHz to 10 MHz in a log-sweep mode.

(Effect of Gas on Electrical Characteristics)

(Comparative Example)

As a comparative example, rectifying characteristics at 400° C. based on the p-n heterojunction of CuO/ZnO are shown in FIG. 3. As shown in FIG. 3, it is difficult to obtain satisfactory discriminativity on CO gas from the conventional DC characteristics. The gas sensor according to the present invention which uses high purity CuO shows a higher discriminativity on the $H_2$ gas mixture than on the CO gas mixture. Also at 250° C. and 300° C., the discriminativity on $H_2$ gas mixture tends to be higher than on the CO gas mixture and it is clarified that it is difficult to obtain satisfactory discriminativity on CO gas from the DC characteristics.

(Present Embodiment)

Figure 4A:
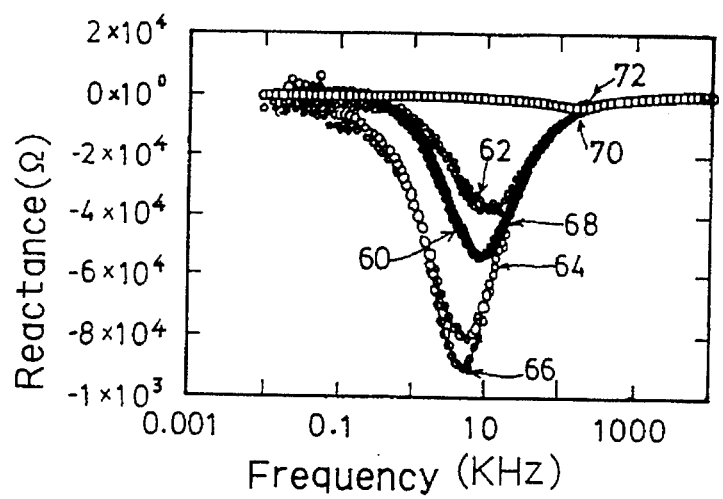
FIGS. 4A, 4B and 4C are graphs showing the frequency dependence and the bias dependence of the reactance (X) which were measured in air, $CO$ gas mixtures and $H_2$ gas mixtures, respectively, at 400° C.
Figure 4B:
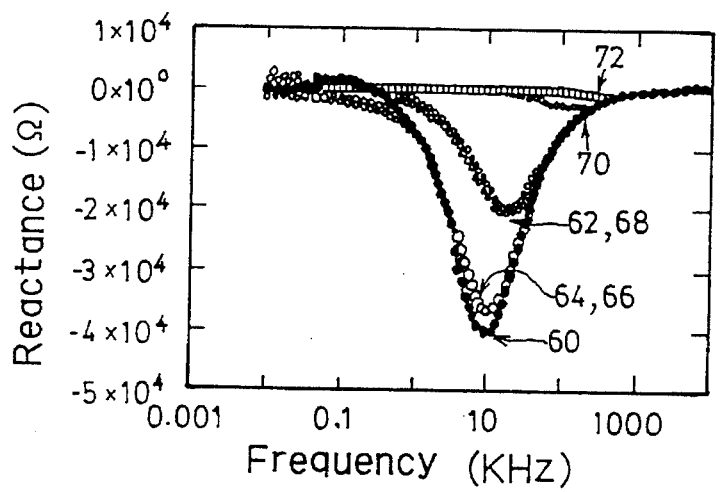
Figure 4C:
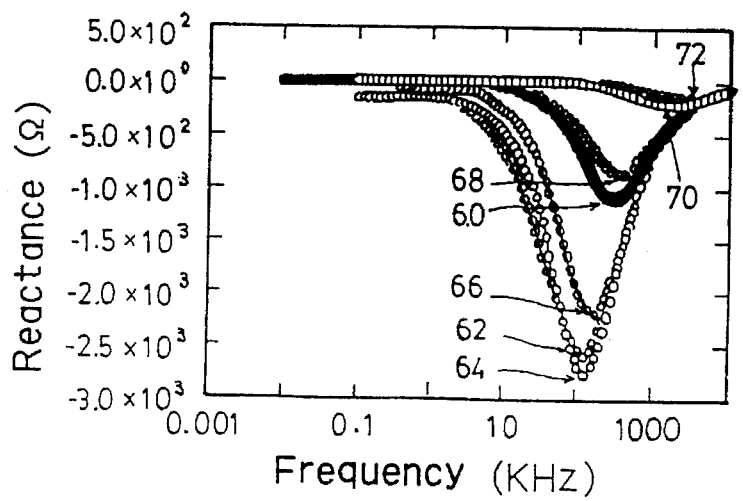

FIGS. 4A, 4B and 4C respectively show the frequency dependence and the bias dependence of the reactance (X) measured at 400° C. respectively in the air, CO gas mixture and $H_2$ gas mixture. Since the reactance is a capacity component given as X<0, the reactance is plotted as a negative value in FIGS. 4 in such manner that the reactance with the bias of 0 V is presented with • (curve 60), curve 62 shows the reactance with the bias of −10 V, curve 64 shows the reactance with the bias of −3 V, curve 66 shows the reactance with the bias of −1 V, curve 68 shows the reactance with the bias of +1 V, curve 70 shows the reactance with the bias of +3 V, and curve 72 shows the reactance with the bias of +10 V.

From FIG. 4, it is known that the frequency dependence and the DC bias dependence of the reactance differs with the kind of gas. As shown in FIG. 4, the frequency dependence and the DC bias dependence of the reactance show the minimum values at a specific frequency, depending on the type of atmosphere gas. Specifically, the values obtained in case of the air are such that the peaks of the values are shifted to the low frequency side when a bias of −1 V to −3 V is applied and the maximum value are obtained when the bias is −1 V (91 kΩ). In the CO mixture gas, the peak of reactance is not likely to be shifted to the low frequency side as shown in FIG. 4B even though a negative bias is applied and the magnitude of the peak tends to decrease. In the $H_2$ mixture gas, the peak of reactance is smallest as shown in FIG. 4C and the peak of reactance with the bias of 0 V is approximately 2% of that in case of the air and shifted to a higher frequency side by 300 kHz or over. However, a mode of variation that the reactance increases with the negative bias and the peak of reactance is shifted to the low frequency side is the same as the reactance in case of the air.

As described above, the mode of variation of the reactance is featured with the bias to be applied and the measuring frequency and therefore it is considered that an objective gas can be discriminated. At 250° C., a remarkable difference depending on the atmosphere gas is not observed in the frequency dependence and the bias dependence of the reactance as compared with that at 400° C.

(Gas Discriminating Method)

The results of measurements of the reactance of the p-n heterojunction of CuO/ZnO at 400° C. as described above are examined as to whether or not the gases can be discriminated.

(1) Bias Dependence under Low Frequency

Figure 5:
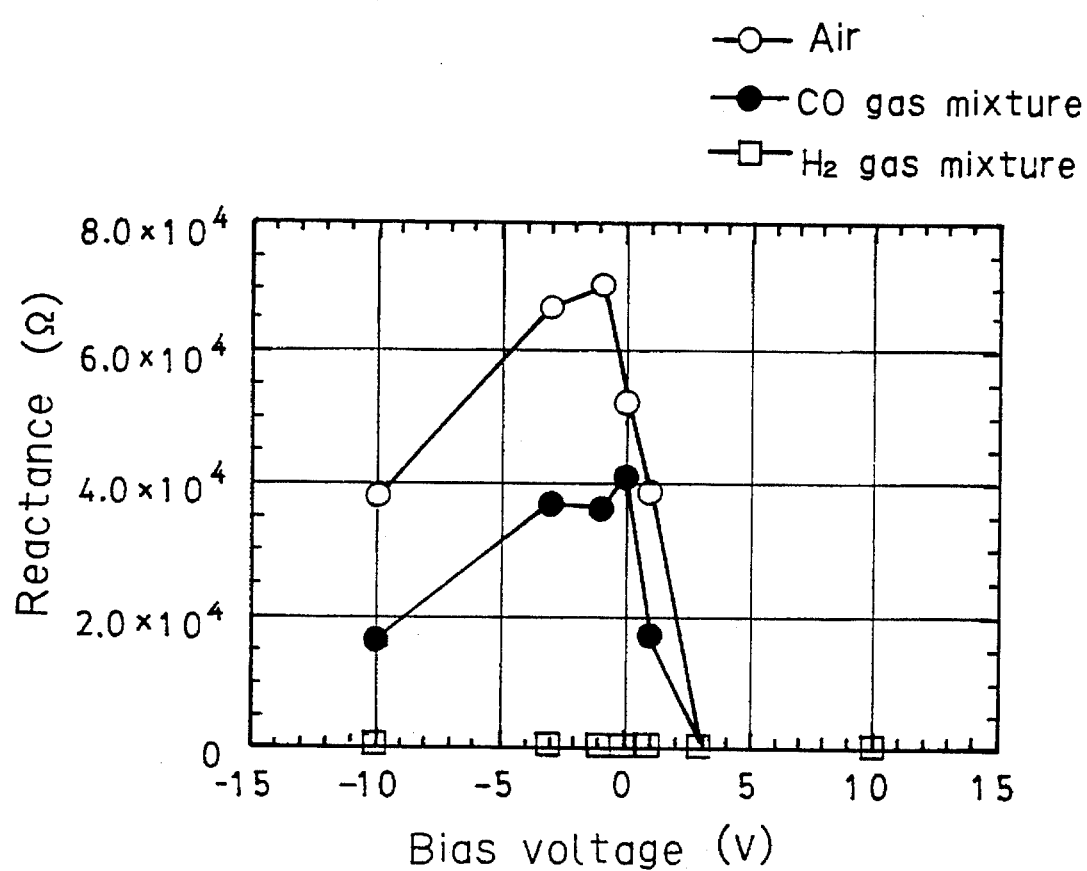
FIG. 5 is a graph showing the DC bias dependence of the absolute value of the reactance measured at 10 kHz in the air, CO gas mixture and $H_2$ gas mixture, respectively.

FIG. 5 shows a graph of the DC bias dependence of the absolute value of the reactance measured at 10 kHz which is plotted with respect to respective atmospheres, that is, air, CO gas mixture and $H_2$ gas mixture. The features of the atmospheres are clearly represented in the area of approximately 0 V bias to the negative bias.

The gas discrimination method is as described below. The absolute value of the reactance reduces under the condition that the bias is 0 V and therefore a reducing gas is detected. When the bias to be applied is changed from 0 V to a negative value (−1 V to −3 V), the absolute value of the reactance further reduces in the CO gas mixture. In the $H_2$ gas mixture, the absolute value of the reactance increases in a monotonous mode as shown in Table 1. In other words, the reactance increases and decreases in opposite directions and therefore the above two kinds of gases can be discriminated.

TABLE 1

|  | Reactance × (kΩ) DC bias voltage (V) | | | |
|---|---|---|---|---|
|  | −10 | −3 | −1 | 0 |
| Air | −37.9 | −66.8 | −70.6 | −52.5 |
| CO (4000 ppm) | −16.5 | −36.9 | −36.2 | −40.9 |
| $H_2$ (4000 ppm) | −0.72 | −0.52 | −0.30 | −0.08 |

(2) Frequency Dependence under Negative Fixed Bias

Figure 6:
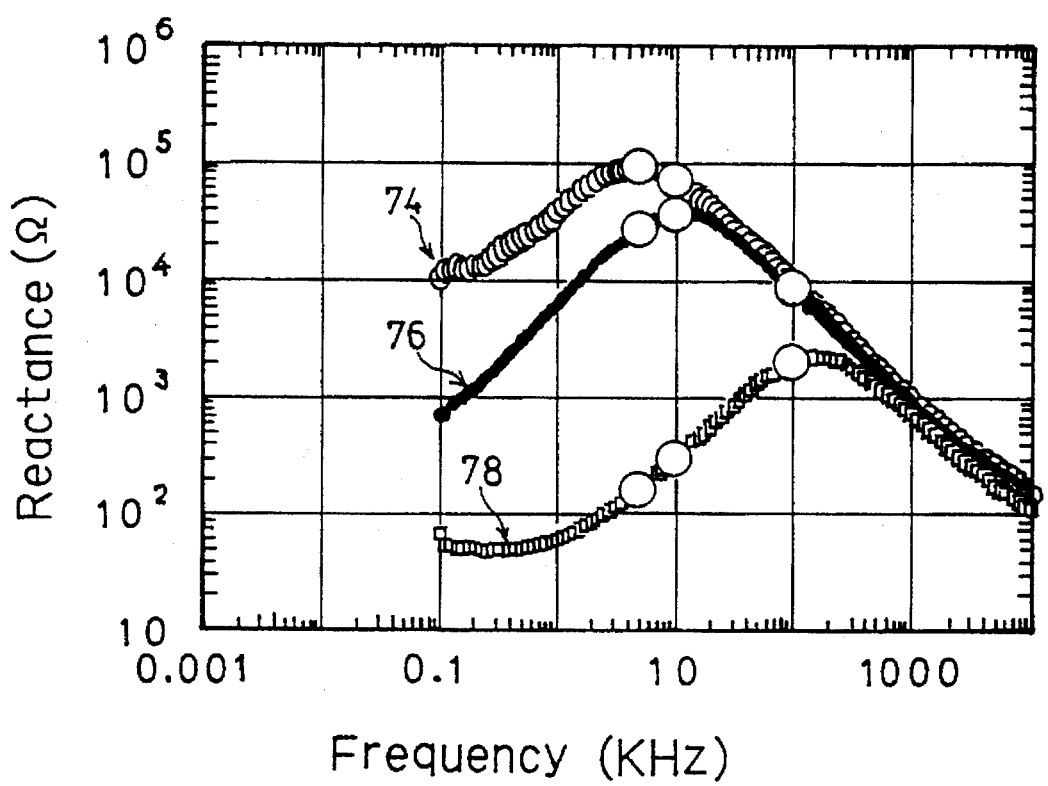
FIG. 6 is a graph showing the frequency bias dependence of the absolute value of the reactance measured with a specified bias of −1 V in the air, CO gas mixture (4000 ppm) and $H_2$ gas mixture (4000 ppm), respectively.

FIG. 6 shows a graph in which the frequency dependence of the absolute value of the reactance measured under a fixed bias voltage of −1 V is plotted with respect to the air, CO gas mixture (4000 ppm) and $H_2$ gas mixture (4000 ppm), respectively, and curves 74, 76 and 78 represent the values in the cases of air, CO gas mixture and $H_2$ gas mixture, respectively. The features of the atmospheres are clearly represented in the high frequency area of 5 kHz or over.

The gas discriminating method is as described below. A reactance at 10 kHz is monitored in reference to the reactance under the bias of −1 V and the frequency of 5 kHz. Though the absolute value of the reactance at 10 kHz in the air lowers below the absolute value of the reactance at 5 kHz, the absolute value of the reactance at 10 kHz increases in the CO gas mixture and the $H_2$ gas mixture. Accordingly, it can be detected that at least one of CO gas and $H_2$ gas is mixed. In this case, if the measuring frequency is increased from 10 kHz to 100 kHz, the absolute value of the reactance decreases in the CO gas mixture but it clearly increases in a monotonous mode in the $H_2$ gas mixture. In other words, it is clarified that the reactance in the range of 10 kHz to 100 kHz increases and decreases in opposite directions, depending on the type of atmosphere gas and therefore the above two kinds of gases can be discriminated. This can be considered that the sensor is tuned up to an appropriate condition for discriminating of a target gas in accordance with a voltage and a frequency from external sources. It is also considered that the capacity component due to adsorption and the variation of resistance at the heterojunction surface differ with the kind of gas and therefore discrimination of the kinds of gases is enabled by detecting this change from AC signals under the negative bias with which the resistance value is increased due to the rectifiability.

[Second Embodiment]

(a) Sensor Head and Specimen

Referring again to FIG. 1, there is shown a sensor head. In this case, CuO (99.9%) and $Na_2CO_3$ (99%) were used as starting material for the p-type oxide semiconductor of the sensor head 10 and $Na_2CO_3$ was doped in CuO so that $Na_2O$ accounts for 1 mole % as the mole percentage. CuO doped with $Na_2CO_3$ was wet-blended in acetone for six hours by using a ball mill, filtered and dried, then calcined in an alumina crucible at 600° C. for three hours. Calcined powder was pulverized again with ethanol as a medium in the mill and dried to produce CuO powder into which $Na_2O$ of 1 mole % wad doped. The p-type oxide semiconductor to be used was made up by molding into a disc with a diameter of 10 mm and a thickness of approximately 1 mm after granulating CuO powder into which $Na_2O$ of 1 mole % was doped in the PVA binder, and fired at 800° C. for three hours. The n-type oxide semiconductor to be used was made up by molding into a disc with a diameter of 10 mm and a thickness of approximately 1 mm after granulating ZnO powder (99.99%) into which $Na_2O$ of 1 mole % was doped in the PVA binder, and fired at 1000° C. for three hours. The relative densities are 98% for ZnO and 85% for CuO.

A silver electrode with an ohmic characteristic is baked on one-side surfaces of respective n-type and p-type semiconductor disc type specimens 12 and 14 which are ground to be parallel with an emery paper (#1000) and these specimens are joined together to form a heterojunction 16. Subsequently, platinum electrode plates 20 to which a lead wire 18 is respectively connected are attached to these specimens 12 and 14 and a heterojunction surface made of p-type/n-type semiconductors is formed by mechanically tightening the specimens through insulation sheets 22 with a stainless steel holder 24. Thus a sensor head 10 having the p-type/n-type semiconductors is made. A thermocouple 26 is prepared to measure a temperature of the sensor head 10.

(b) Measuring Method

Referring again to FIG. 2, there is shown a construction of the gas sensor. The sensor head 10 is set in a ceramics tube 30 and air, a mixture of air and CO gas (4000 ppm) and a mixture of air and $H_2$ gas (4000 ppm) are separately let to flow into the ceramics tube 30 at a flow rate of 200 ml/min (room temperature). The air, CO gas and $H_2$ gas are separately introduced into the ceramics tube 30 from respective gas cylinders 32, 34 and 36 through flow meters 38 and 40 and valves 42, 44 and 46. The sensor head 10 is heated in a range of room temperature to 400° C. in a furnace 50 provided with a heater 48. Under a condition where the sensor head 10 is maintained at, for example, 400° C., the gases described above are introduced and DC voltage/current characteristic (HP) and a DC bias are applied to the sensor head 10. The voltage and current of the sensor head 10 are measured by a voltmeter (YOKOGAWA 7651) 52 and an ammeter (YOKOGAWA 7562) 54 and a complex impedance (HP4192A) is measured by using a low frequency impedance analyzer 56. These units of measuring equipment are controlled by a personal computer 58, and a resistance component (R) and a reactance component (X) of the complex impedance Z (=R+jX) are measured from 0.01 kHz to 10 MHz in a log-sweep mode.

(Effect of Gas on Electrical Characteristics)

An embodiment of the gas discriminating method using the above-described gas sensor is shown below with a comparative example.

(Comparative Example)

Figure 7:
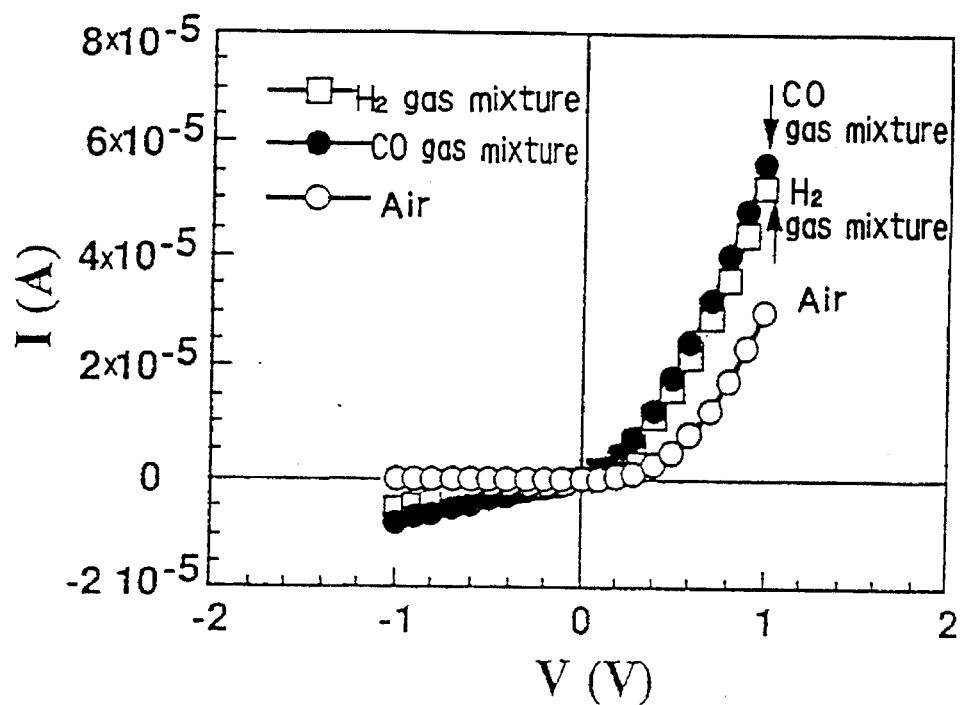
FIG. 7 is a graph of a comparison example showing the rectifying characteristics at 250° C. by means of the hetero p-n junction of CuO/ZnO.
Figure 8:
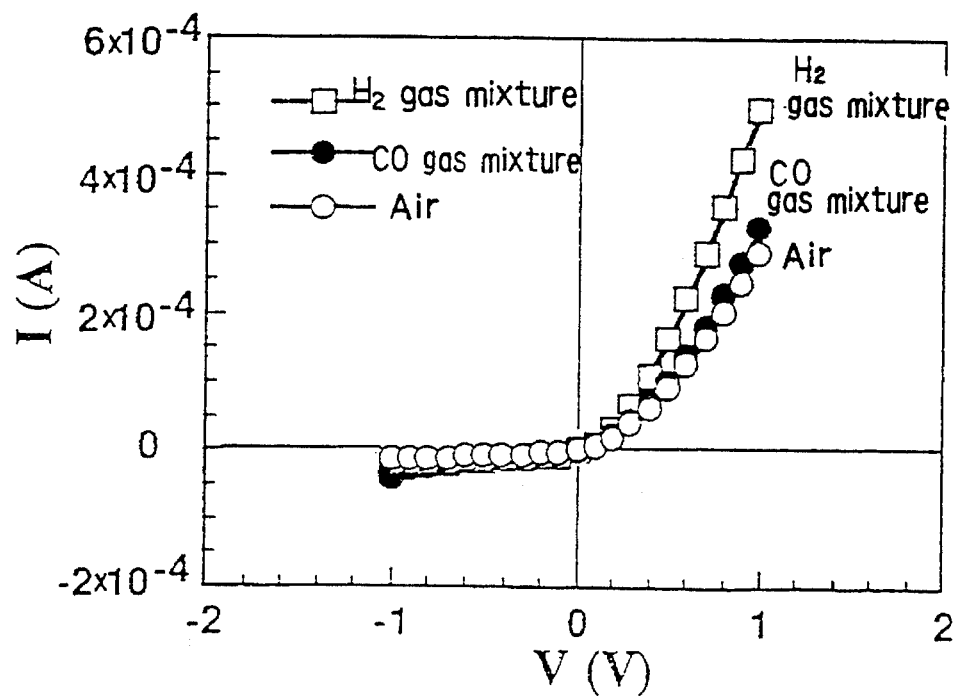
FIG. 8 is a graph of a comparison example showing the rectifying characteristics at 400° C. by means of the hetero p-n junction of CuO/ZnO.

FIGS. 7 and 8 respectively show the rectifying characteristics by means of the p-n heterojunction of CuO/ZnO into which $Na_2O$ of 1 mole % is doped at 250° C. and 400° C. This system which uses CuO into which $Na_2O$ of 1 mole % was doped showed a substantially equivalent high selectivity on the CO gas mixture and the $H_2$ gas mixture at 250° C. as shown in FIG. 7. The system showed a higher selectivity on the $H_2$ gas mixture at 400° C. than on the CO gas mixture as shown in FIG. 8. It is considered that it is difficult to obtain a satisfactory selectivity only on CO gas from the DC characteristics at either of the temperatures.

(Present Embodiment)

Figure 9A:
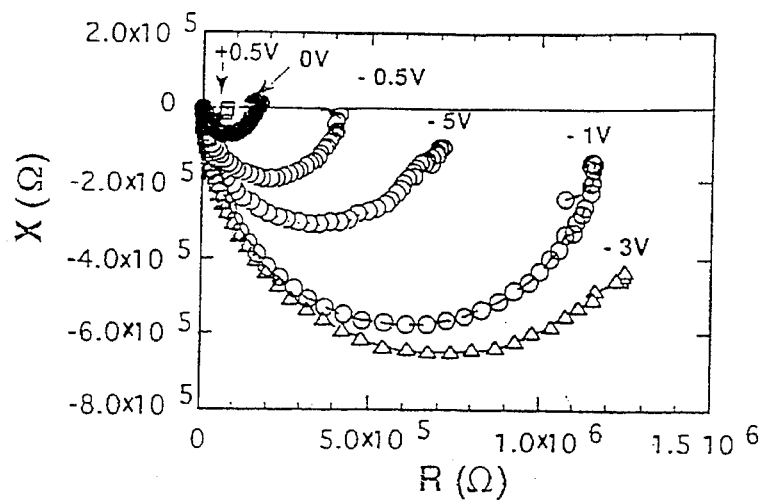
FIGS. 9A, 9B and 9C are respectively a graph showing the bias dependence of the real number part R and the imaginary number part X, which are plotted with frequencies as parameters, of the impedances (Z=R+jX) which were measured in air, CO gas mixtures and $H_2$ gas mixtures at 250°.
Figure 9B:
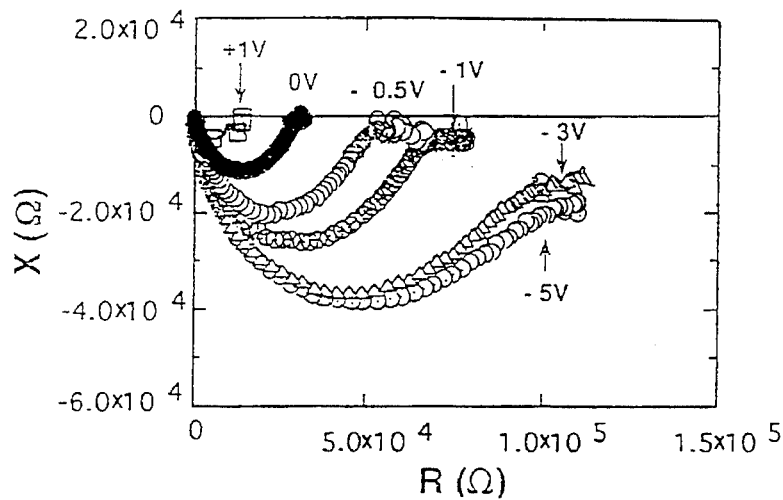
Figure 9C:
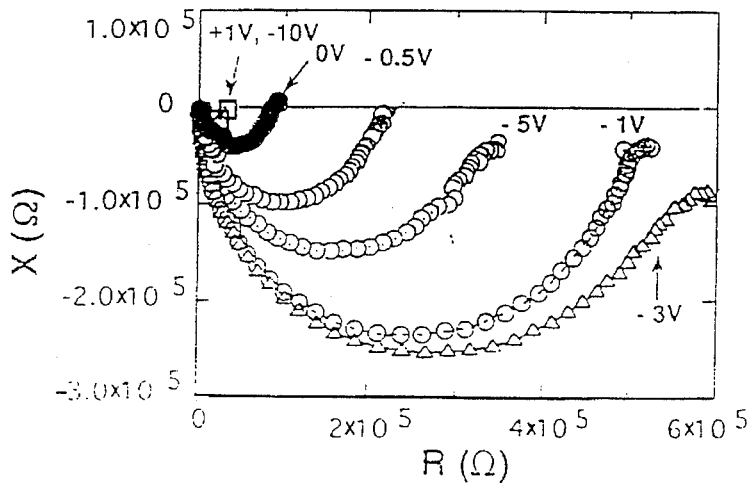

FIGS. 9A, 9B and 9C respectively show a bias dependence of the real number part R and the imaginary number part X of the impedance which is measured at 250° C. in the air, CO gas mixture and $H_2$ gas mixture and plotted with a frequency as a parameter (call-call plotting). Since the reactance is produced by the capacity component and represented by X<0, it is plotted as a negative value in the diagrams. The plot shows a semi-circle. A difference resulting from the kind of gas is found in the dependence of the reactance component on the frequency and the DC bias.

Figure 10:
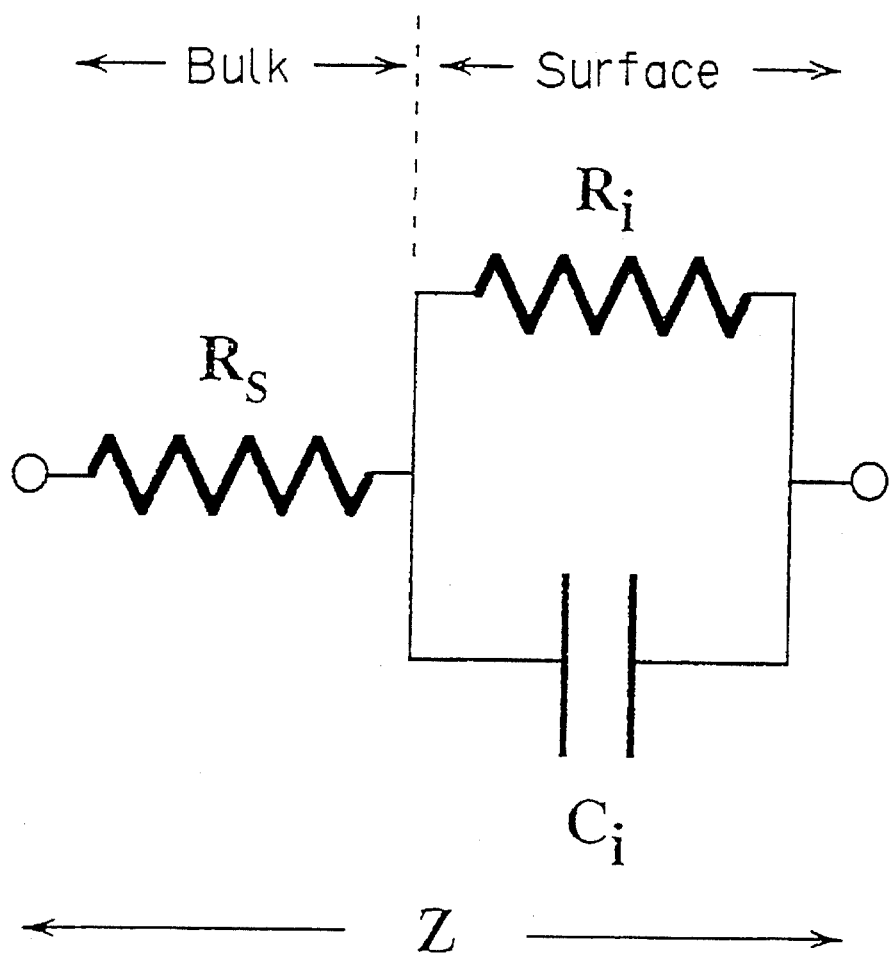
FIG. 10 is a circuit diagram showing an electrically equivalent circuit of the heterojunction surface.

An electric equivalent circuit of the heterojunction surface is shown in FIG. 10.

Figure 11:
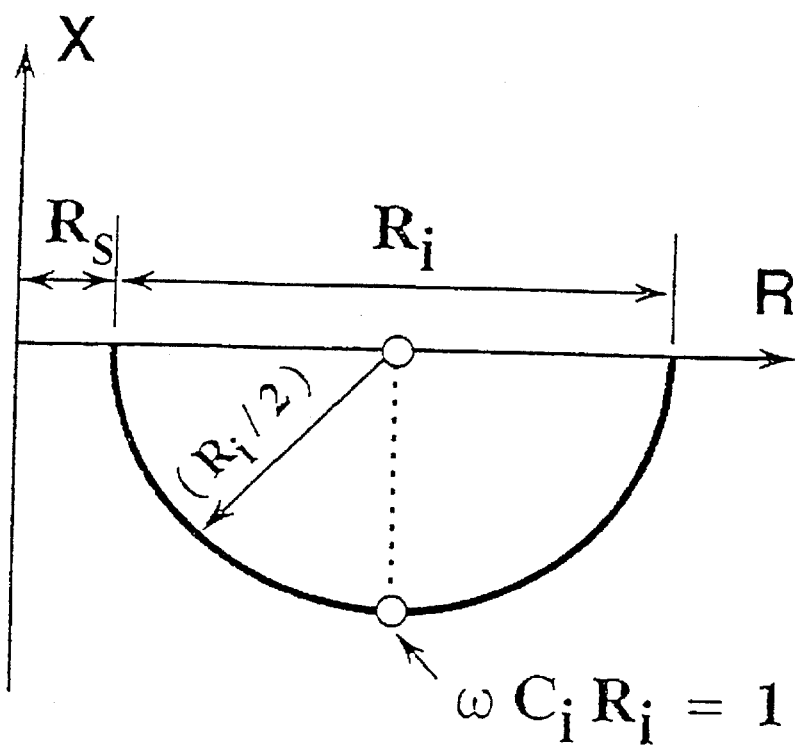
FIG. 11 is a graph showing the plotting of the real number part to the imaginary number part of the impedance in the electrically equivalent circuit shown in FIG. 10 and the equivalent circuit components thereof.

The electric equivalent circuit of the hetero junction surface, as shown in FIG. 10, is provided with a parallel junction of the surface resistance Ri and the capacity Ci on the surface and the resistance Rs of the bulk is connected to this parallel junction. Respective components can be obtained from plotting on the diagram as shown in FIG. 11. Data at the high frequency side of the plot is converged to the origin of the axis and can be actually treated as Rs<Ri.

Figure 12:
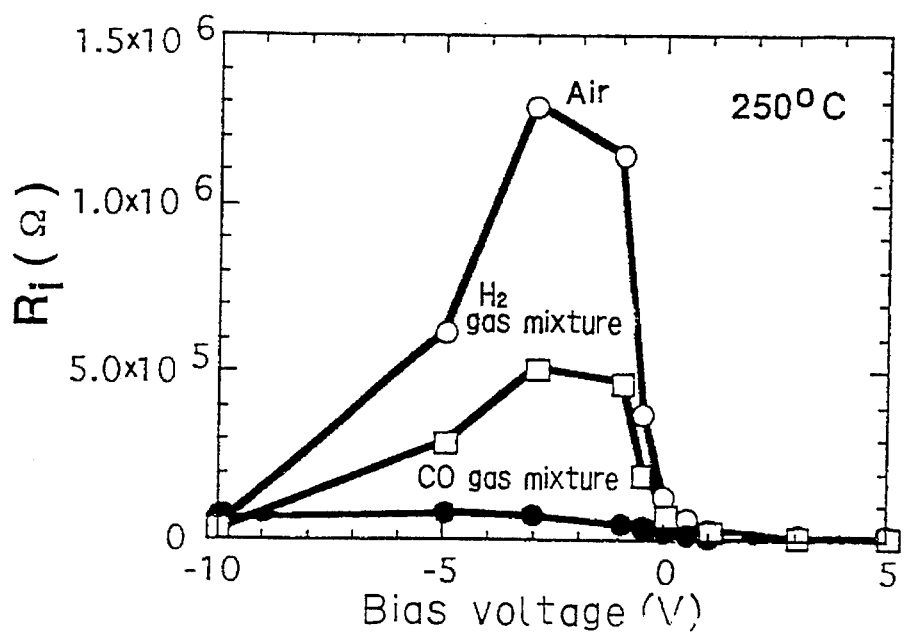
FIG. 12 is a graph showing the results of measurement as to the bias dependence of the surface resistance Ri of the equivalent circuit resistance component at the surface of the heterojunction formed with CuO and ZnO to which $Na_2O$ of 1 mole % is doped, in air, CO gas mixture (4000 ppm) and $H_2$ gas mixture, respectively, at 250° C.
Figure 13:
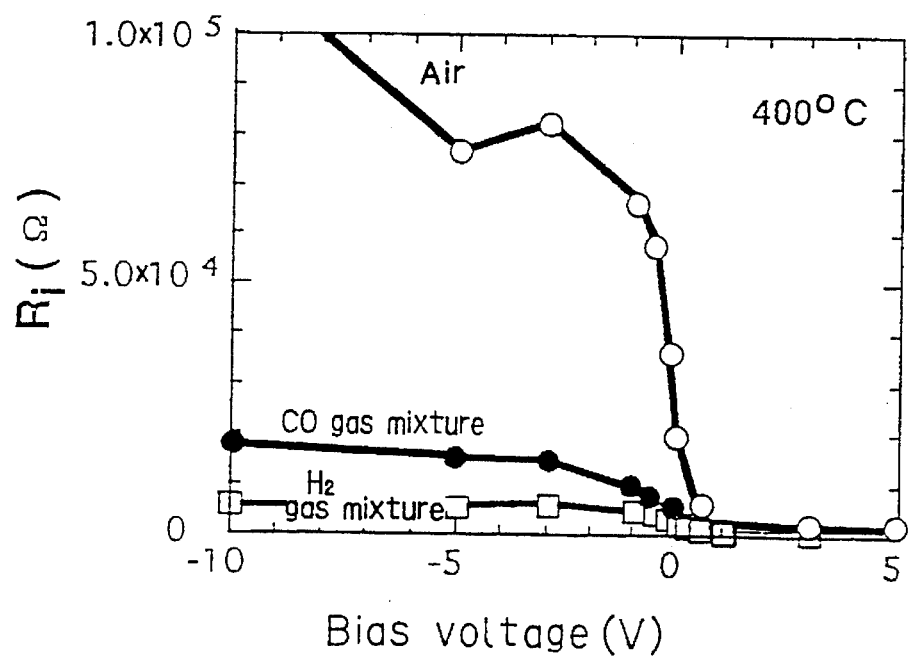
FIG. 13 is a graph showing the results of measurement as to the bias dependence of the surface resistance Ri of the equivalent circuit resistance component at the surface of the heterojunction formed with CuO and ZnO to which $Na_2O$ of 1 mole % is doped, in air, CO gas mixture (4000 ppm) and $H_2$ gas mixture, respectively at 400° C.
Figure 14:
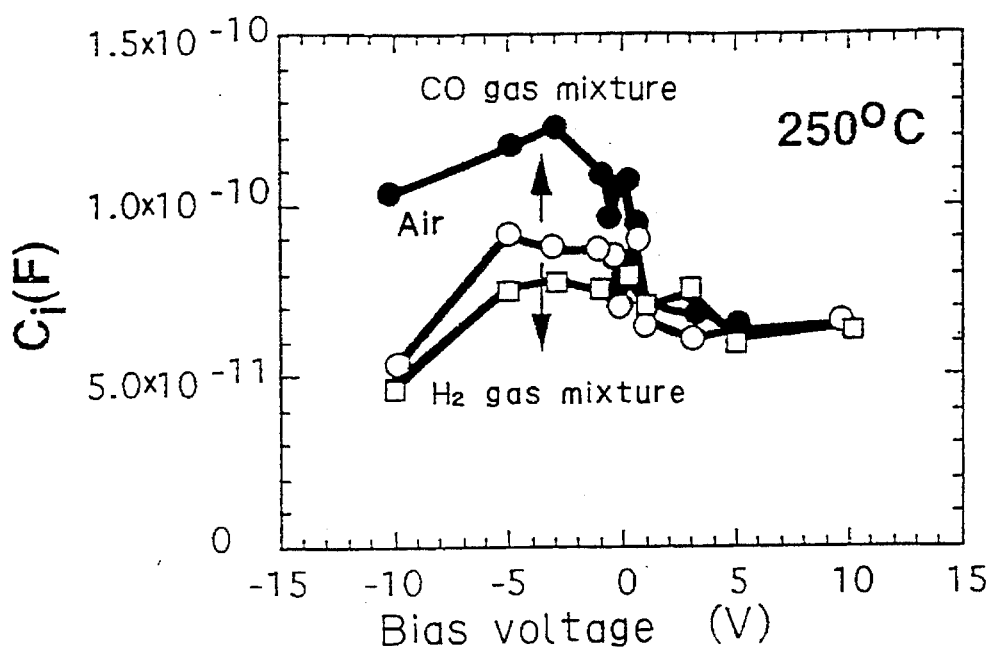
FIG. 14 is a graph showing the results of measurement as to the bias dependence of the capacity Ci of the equivalent circuit resistance component at the surface of the heterojunction formed with CuO and ZnO to which $Na_2O$ of 1 mole % is doped, in air, CO gas mixture (4000 ppm) and $H_2$ gas mixture, respectively, at 250° C.
Figure 15:
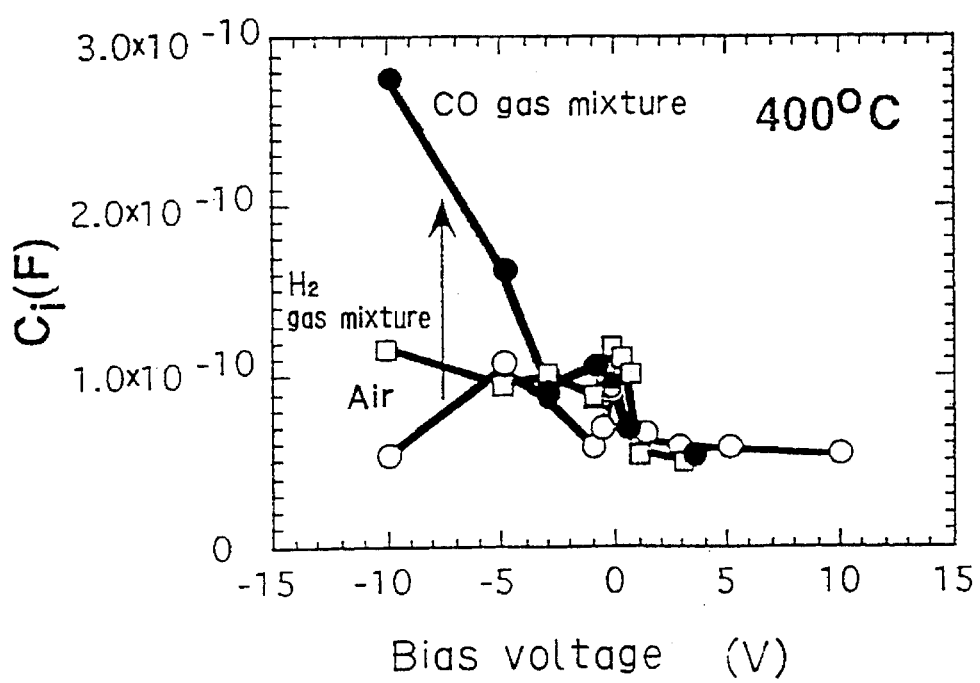
FIG. 15 is a graph showing the results of measurement as to the bias dependence of the capacity Ci of the equivalent circuit resistance component at the surface of the heterojunction formed with CuO and ZnO to which $Na_2O$ of 1 mole % is doped, in air, CO gas mixture (4000 ppm) and $H_2$ gas mixture, respectively, at 400° C.

FIGS. 12 and 13 show the relationship between the bias voltage and the surface resistance Ri obtained at 250° C. and 400° C., respectively, and FIGS. 14 and 15 show the relationship between the bias voltage and the capacity Ci obtained at 250° C. and 400° C., respectively.

As shown in FIG. 12, the resistance in the CO gas mixture at 250° C. is minimized by addition of Na. As shown in FIG. 14, the variation of the capacity increases in the CO gas mixture but decreases in the $H_2$ gas mixture. As shown in FIG. 14, the kind of gas can be discriminated by using the difference of the static capacity.

On the other hand, this tendency changes at 350° C. or a higher temperature. As shown in FIG. 13, the resistance is minimum in the $H_2$ gas mixture and, as shown in FIG. 15, the capacity in the $H_2$ gas mixture becomes equivalent to the capacity in air or larger than in air and changes in the same direction as in the CO gas mixture.

Thus, the equivalent circuit component is featured in a mode of variation and it is assumed that an objective gas can be discriminated. The above-described tendency is observed in the range of the density of $Na_2O$ to be doped from 0.2 mole % to 5 mole %. Particularly, this tendency is remarkable in the range from 0.4 mole % to 3 mole %.

(d) Gas Discriminating Method

Whether a gas can be discriminated was examined from the result of measurement of the reactance at 250° C. of p-n joint the above equivalent circuit component has.

(1) Bias Dependence Under the Specified Frequency

Figure 16:
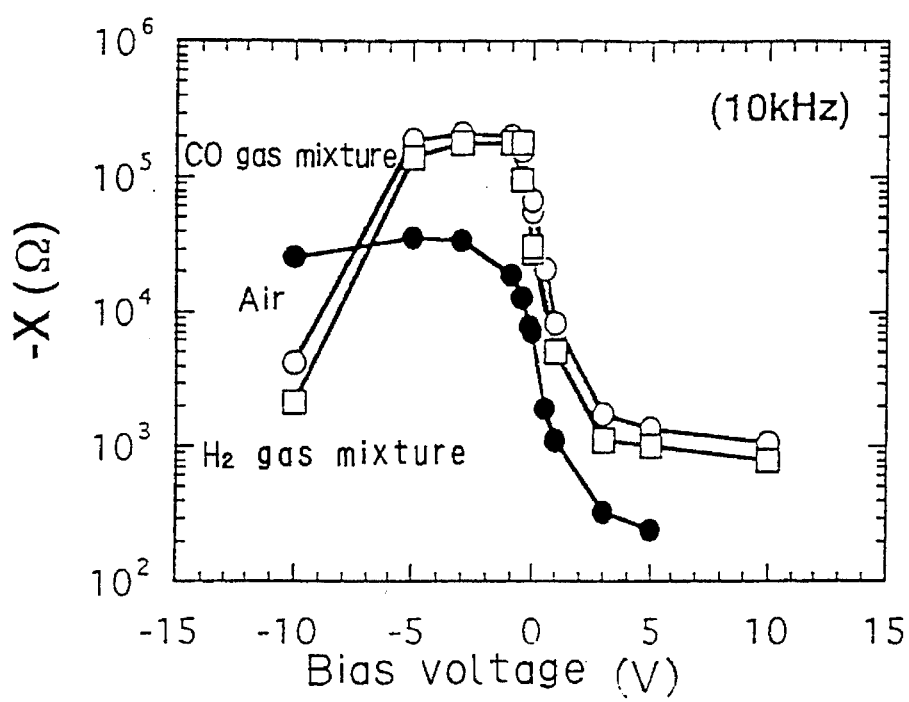
FIG. 16 is a graph showing the results of measurement as to the bias dependence of the reactance component (X) measured at 10 kHz of the heterojunction sensor formed with CuO and ZnO to which $Na_2O$ of 1 mole % is doped, in air, CO gas mixture (4000 ppm) and $H_2$ gas mixture, respectively, at 250° C.
Figure 17:
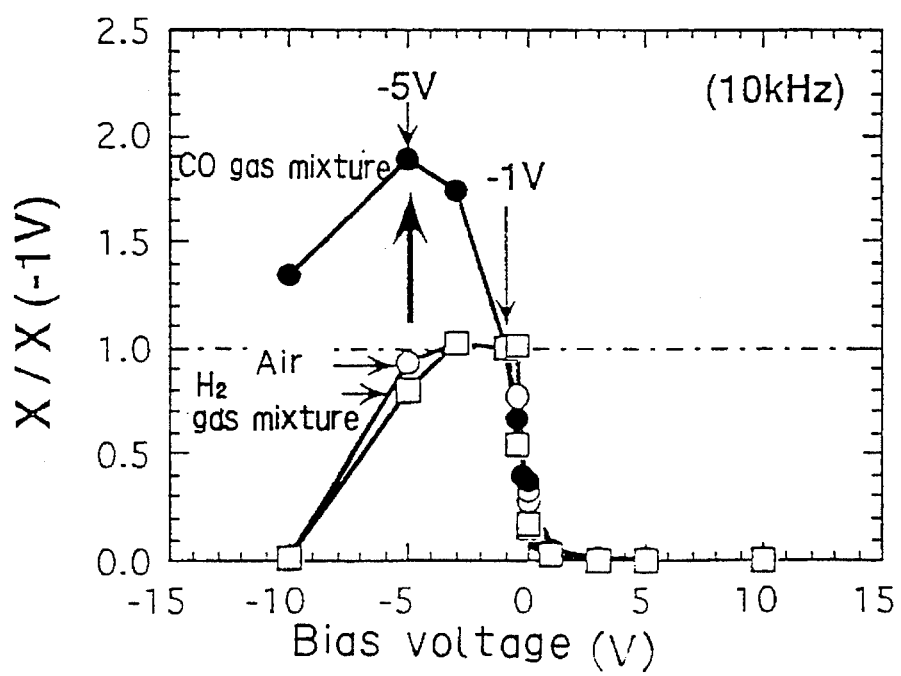
FIG. 17 is a graph showing the results of measurement as to the bias dependence of a value, which is obtained by standardizing, with a reactance at −1 V, the reactance component (X) measured at 10 kHz of the heterojunction sensor formed with CuO and ZnO to which $Na_2O$ of 1 mole % is doped, in air, CO gas mixture (4000 ppm) and $H_2$ gas mixture, respectively, at 250° C.

FIG. 16 shows the DC bias dependence of the absolute value of the reactance measured with 10 kHz in respective atmospheric gases, indicating that the reactance measured in the CO gas mixture is lower than that measured in other two kinds of gases. The reactance in the CO gas mixture is reduced to ⅑ of that in air and the hydrogen gas mixture. Accordingly, it is known that CO gas can be selectively discriminated by utilizing the decrease of the reactance under, for example, the bias voltage of −1 V. FIG. 17 shows the reactance in respective atmospheric gases in reference to the reactance measured under the voltage of −1 V.

When the bias is applied from −1 V to a negative voltage (−3 V to −5 V), the absolute value of the reactance reduces in a monotonous mode in the air and the $H_2$ gas mixture while the reactance value increases only in the CO gas mixture. In other words, it is known that the above two kinds of gases can be discriminated since the reactance increases and decreases in opposite directions. In the case of 400° C. for which high purity CuO into which Na is not doped is used, the reactance changes in a direction opposite to that in the case of 250° C. According to this discriminating method, the kind of gas can be discriminated from the reactance when $Na_2O$ to be doped is 0.2 mole % to 5 mole % as shown in FIG. 17.

(2) Frequency Dependence Under the Negative Bias Voltage

Figure 18:
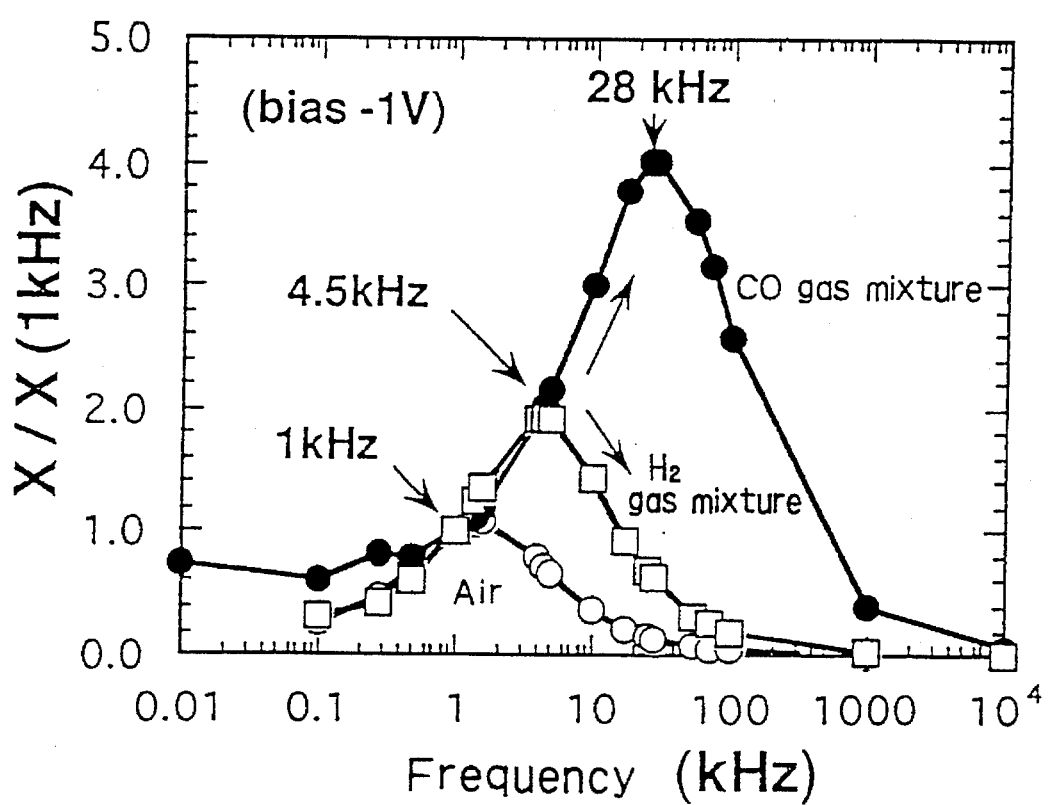
FIG. 18 is a graph showing the results of measurement as to the frequency dependence of a value, which is obtained by standardizing, with a reactance at 1 kHz, the reactance component (X) measured at −1 V of the heterojunction sensor formed with CuO and ZnO to which $Na_2O$ of 1 mole % is doped, in air, CO gas mixture (4000 ppm) and $H_2$ gas mixture, respectively, at 250° C.

FIG. 18 shows a graph which represents the frequency of the reactance measured under a fixed bias of −1 V in respective atmospheric gases by standardization in reference the reactance measured with 1 kHz.

Though the value of reactance reduces in a monotonous mode in a normal air after the frequency has increased over 1 kHz, the reactance value increases up to 4.5 kHz in a reducing gas (in this case, $H_2$ gas mixture and CO gas mixture) and therefore this increase can be detected. In this case, if the measuring frequency is increased from 4.5 kHz to 28 kHz, the absolute value of the reactance decreases in the $H_2$ gas mixture but the reactance clearly increases and reaches the peak at 28 kHz in the CO gas mixture. Specifically, it is known that the reactance measured in the range of 4.5 kHz to 28 kHz increases and decreases in opposite directions, depending on the kind of the atmospheric gas and therefore the above two kinds of can be discriminated. In addition, in the system using CuO to which Na is added, the peak of reactance in the CO gas mixture remains at a higher frequency side than that in the $H_2$ gas mixture and this is convenient for discrimination of air. This can be considered as if a state of an appropriate gas sensor for discriminating a target gas is tuned up in accordance with a voltage and frequency applied from the external source.

It is considered that the capacity component by adsorption and the variation of resistance change depending on the kind of gas and discrimination of the kinds of gases is enabled by detecting this change according to AC signals under the negative voltage with which the resistance value is increased by rectifiability.

As shown in this case, CO gas could be discriminated at a low temperature below 350° C. by doping $Na_2O$ in CuO. In a case that no doping is made, CO gas can be discriminated at 400° C. Discrimination as described above is enabled in a range of the doping quantity of $Na_2O$ from 0.2 mole % to 5 mole %.

Based on a similar way of thinking, discrimination of CO gas was examined with respect to CuO into which $Li_2O$ and $K_2O$ of 0.1, 0.2, 0.5, 1, 2, 3, 5, 8 or 10 mole % are doped. As shown in FIGS. 17 and 18, discrimination of CO is possible in the range of 0.2 mole % to 5 mole % owing to addition of $Na_2O$.

What is claimed is:

1. A gas sensor comprising:

a sensor head having a p-type oxide semiconductor and an n-type oxide semiconductor on which a junction part is formed by hetero-joining end surfaces thereof;

signal applying means for applying AC signals onto which a DC bias is superposed to said junction part; and impedance measuring means for measuring impedance characteristics of said junction part.

2. A gas sensor according to claim 1, wherein said p-type oxide semiconductor and said n-type oxide semiconductor are respectively made of ceramics.

3. A gas sensor according to claim 1, wherein said p-type oxide semiconductor is CuO and said n-type oxide semiconductor is ZnO.

4. A gas sensor according to claim 3, wherein an alkali metal is doped in said CuO.

5. A gas sensor according to claim 4, wherein said alkali metal is selected from the group consisting of Li, Na and K and a doping quantity is within a range of 0.2 mole $\% \leq M_2O \leq 5$ mole %, where M is Li, Na or K.

6. A gas discriminating method comprising:

a step for applying a DC bias and AC signals which are superposed to a junction part, which is formed on a gas sensor having a p-type oxide semiconductor and an n-type oxide semiconductor by means of heterojunction of end surfaces thereof, and measuring an impedance characteristic of said junction part; and a step for discriminating a kind of gas in accordance with a dependence on a frequency of said AC signals and on said DC bias of said impedance characteristic.

7. A gas discriminating method comprising:

a step for applying a DC bias, which makes a p-type oxide semiconductor provided on a gas sensor negative and an n-type oxide semiconductor provided on said gas sensor positive under a specified frequency, to a junction part of the gas sensor having said p-type oxide semiconductor and said n-type oxide semiconductor, which is formed by means of heterojunction of end surfaces thereof, and measuring an impedance characteristic of said junction part; and a step for discriminating a kind of gas in accordance with a dependence on said DC bias of a reactance component of said impedance characteristic.

8. A gas discriminating method comprising:

a step for applying a predetermined DC bias, which makes a p-type oxide semiconductor provided on a gas sensor negative and an n-type oxide semiconductor provided on said gas sensor positive, and AC signals to a junction part of the gas sensor having said p-type oxide semiconductor and said n-type oxide semiconductor, which is formed by means of heterojunction of end surfaces thereof, and measuring an impedance characteristic of said junction part by varying the frequency of said AC signals; and a step for discriminating a kind of gas in accordance with a dependence on said frequency of a reactance component of said impedance characteristic.

9. A gas discriminating method comprising:

a step for applying a DC bias and AC signals which are superposed to a junction part, which is formed on a gas sensor having a p-type oxide semiconductor and an n-type oxide semiconductor by means of heterojunction of end surfaces thereof, and measuring an impedance characteristic of said junction part; and a step for discriminating CO gas and $H_2$ gas in accordance with a dependence on a frequency of said AC signals and on said DC bias of said impedance characteristic.

* * * * *